United States Patent
Bharat et al.

(10) Patent No.: US 9,700,737 B2
(45) Date of Patent: Jul. 11, 2017

(54) BRACHYTHERAPY APPARATUS

(71) Applicant: KONINKLIJKE PHILIPS N.V., Eindhoven (NL)

(72) Inventors: Shyam Bharat, Cortlandt Manor, NY (US); Christopher Stephen Hall, Kirkland, WA (US); Cynthia Ming-Fu Kung, New York, NY (US); Jochen Kruecker, Washington D.C., DC (US)

(73) Assignee: Koninklijke Philips N.V., Eindhoven (NL)

( * ) Notice: Subject to any disclaimer, the term of this patent is extended or adjusted under 35 U.S.C. 154(b) by 274 days.

(21) Appl. No.: 14/398,851

(22) PCT Filed: May 3, 2013

(86) PCT No.: PCT/IB2013/053542
§ 371 (c)(1),
(2) Date: Nov. 4, 2014

(87) PCT Pub. No.: WO2013/171615
PCT Pub. Date: Nov. 21, 2013

(65) Prior Publication Data
US 2015/0119628 A1     Apr. 30, 2015

Related U.S. Application Data

(60) Provisional application No. 61/646,951, filed on May 15, 2012.

(51) Int. Cl.
*A61N 5/10*       (2006.01)
(52) U.S. Cl.
CPC ........... *A61N 5/1007* (2013.01); *A61N 5/103* (2013.01); *A61N 5/1027* (2013.01);
(Continued)

(58) Field of Classification Search
CPC .. A61N 5/1001; A61N 5/1002; A61N 5/1007; A61N 5/1014; A61N 5/1027;
(Continued)

(56) References Cited

U.S. PATENT DOCUMENTS

| 4,122,838 A | 10/1978 | Leonard |
| 8,036,436 B2 | 10/2011 | Geiger et al. |

(Continued)

FOREIGN PATENT DOCUMENTS

| WO | 2011080606 A1 | 7/2011 |
| WO | 2012001551 A1 | 1/2012 |

OTHER PUBLICATIONS

Cury et al : "Prostate Gland Edema After Single-Fraction High-Dose Rate Brachytherapy Before External Beam Radiation Therapy"; Brachytherapy 9 (2010), pp. 208-212.
(Continued)

*Primary Examiner* — Charles A Marmor, II
*Assistant Examiner* — Thaddeus Cox

(57) ABSTRACT

The invention relates to a brachytherapy apparatus (1) for applying a brachytherapy to a living object. The brachytherapy apparatus comprises a planning unit (14) for determining a placing plan defining placing positions and placing times for one or several radiation sources within the living object and close to a target region. The placing plan is determined such that the placing times are within a treatment time window determined by a treatment time window determination unit (13), wherein within the treatment time window a change of a spatial parameter of the living object caused by swelling is minimized. An adverse influence on the brachytherapy due to swelling can thereby be minimized, which improves the quality of the brachytherapy.

15 Claims, 7 Drawing Sheets

(52) U.S. Cl.
CPC ......... *A61N 5/1037* (2013.01); *A61N 5/1049* (2013.01); *A61N 2005/1058* (2013.01)

(58) Field of Classification Search
CPC ...... A61N 2005/1008; A61N 2005/101; A61N 2005/1011; A61N 2005/1012; A61N 2005/1018; A61N 2005/1019; A61N 2005/1024; A61N 2005/1025
See application file for complete search history.

(56) References Cited

U.S. PATENT DOCUMENTS

| | | |
|---|---|---|
| 8,328,723 B2 | 12/2012 | Azuma et al. |
| 8,366,597 B2 | 2/2013 | Hentrich et al. |
| 8,721,514 B2 | 5/2014 | Shechter |
| 2003/0065260 A1 | 4/2003 | Cheng et al. |
| 2004/0228509 A1 | 11/2004 | Holupka et al. |
| 2015/0119628 A1 | 4/2015 | Bharat et al. |

OTHER PUBLICATIONS

Kiffer et al: "Impact of OEDEMA on Implant Geometry and Dosimetry for Temporary High Dose Rate Brachytherapy of the Prostate"; Australasian Radiology (2003), 47, pp. 172-176.

Sloboda et al: "Time Course of Prostatic Edema Post Permanent Seed Implant Determined by Magnetic Resonance Imaging"; Brachytherapy 9 (2010) pp. 354-361.

Taussky et al: "Sequential Evaluation of Prostate Edema After Permanent Seed Prostate Brachytherapy Using CT-MRI Fusion"; In. J. Radiation Oncology Biol. Phys., vol. 62, No. 4, pp. 974-980, 2005.

BRACHYTHERAPY APPARATUS

CROSS-REFERENCE TO PRIOR APPLICATIONS

This application is the U.S. National Phase application under 35 U.S.C. §371 of International Application Serial No. PCT/IB2013/053542, filed on May 3, 2013, which claims the benefit of U.S. Provisional Application Ser. No. 61/646951, filed on May 15, 2013. These applications are hereby incorporated by reference herein.

FIELD OF THE INVENTION

The invention relates to a brachytherapy apparatus, a brachytherapy method and a computer program for applying a brachytherapy to a living object.

BACKGROUND OF THE INVENTION

WO 2011/080606 A1 discloses a brachytherapy apparatus comprising an applicator having at least one radiation source or seed receiving channel configured for being implanted in soft tissue adjacent a target region to be irradiated. The brachytherapy apparatus further comprises a means for generating a high resolution planning image of the target region including the applicator, wherein the high resolution planning image is used for determining a three-dimensional treatment plan. A tracking device tracks a position of the applicator relative to the target region, wherein the tracking device is configured to track the position of the applicator by measuring, via shape sensing, a location and a shape of the at least one radiation source or seed receiving channel.

During and after the at least one radiation source or seed receiving channel has been implanted in the soft tissue, the soft tissue swells, thereby modifying the position of the at least one radiation source or seed receiving channel relative to the target region. This changing of the relative position can reduce the quality of the brachytherapy.

SUMMARY OF THE INVENTION

It is an object of the present invention to provide a brachytherapy apparatus, a brachytherapy method and a computer program for applying a brachytherapy to a living object, wherein the quality of the brachytherapy can be improved.

In a first aspect of a present invention a brachytherapy apparatus for applying a brachytherapy to a living object is presented, wherein the brachytherapy apparatus comprises:
  a radiation source emitting radiation,
  a placing unit for being inserted into the living object and for placing the radiation source close to a target region of the living object for directing the emitted radiation to the target region, wherein the living object swells when the placing unit is inserted into the living object,
  an imaging unit for generating images of the living object over time,
  a spatial parameter determination unit for determining a spatial parameter of the living object, which changes over time with the swelling of the living object, from the generated images of the living object,
  a treatment time window determination unit for determining a treatment time window, in which a change of the spatial parameter of the living object is minimal,
  a planning unit for determining a placing plan defining placing positions within the living object at which the radiation source is to be placed and placing times defining when and how long the radiation source is to be placed at the respective placing position based on the generated images and the determined treatment time window, wherein the planning unit is adapted to determine the placing plan such that the placing times are within the treatment time window.

Since the treatment determination unit determines a treatment time window, in which a change of the spatial parameter of the living object, which is caused by the swelling of the living object, is minimal and since the planning unit determines the placing plan such that the placing times are within the treatment time window, a brachytherapy performed in accordance with the placing plan applies the radiation to the target region while a modification of a relative position of the radiation source and the target region caused by swelling of the living object is minimal, in particular, not present at all. The radiation source can therefore be placed relative to the target region reliably at a desired position for accurately treating the target region, thereby improving the quality of the brachytherapy.

The living object is preferentially a part of a person or of an animal like an organ, for instance, the prostate. The target region is preferentially a tumor region of the part of the person. In order to place the radiation source close to the target region, it can be placed adjacent to or within the target region.

The placing unit is preferentially adapted to place one or several radiation sources at different placing positions within the living object for performing the brachytherapy. The planning unit is preferentially adapted to plan the different placing positions and corresponding placing times defining when and how long the respective radiation source dwells at the respective placing position.

The placing unit can comprise one or several catheters for inserting one or several radiation sources into the living object close to the target region. Moreover, the placing unit preferentially further comprises one or several navigation elements to which the radiation sources are attached, wherein a respective navigation element can be moved within a respective catheter for placing the respective radiation source attached to the respective navigation element at the respective placing position. The navigation elements are preferentially wires to which the radiation sources are attached.

The radiation source is preferentially a radioactive radiation source emitting radioactive radiation like Ir-192, and the swelling is generally a progressing edema caused by the insertion of the placing unit into the living object.

The spatial parameter is, for instance, the volume or the shape of the living object. For example, the treatment time window determination unit can be adapted to determine the treatment time window such that it contains a minimum of a volume change. In particular, the treatment time window determination unit can be adapted such that the volume of the living object does substantially not change in the treatment time window. Alternatively or in addition, the treatment time window determination unit can be adapted to determine the treatment time window such that it contains a minimum of a shape change. For instance, the treatment time window determination unit can be adapted such that the shape of the living object does substantially not change in the treatment time window.

The imaging unit is preferentially adapted to generate a three-dimensional image of the living object. In another embodiment the imaging unit can also be adapted to generate a two-dimensional image. Moreover, the imaging unit is preferentially adapted to generate an ultrasound image or a magnetic resonance image.

The brachytherapy apparatus can comprise a control unit for controlling the placing unit depending on the determined placing plan. Alternatively, the placing unit may be placed manually in accordance with the determined placing plan.

In a preferred embodiment the treatment time window determination unit is adapted to a) provide predefined swelling rules defining an estimated future change of the spatial parameter caused by swelling based on an actual change of the spatial parameter, b) estimate a future change of the spatial parameter caused by swelling based on the predefined rules and the determined spatial parameter of the living object, and c) determine the treatment time window based on the estimated future change of the spatial parameter. The treatment time window can therefore be determined, before a minimum of a change of the spatial parameter of the living object has been reached, thereby allowing the planning unit to plan the placing plan such that the placing times are within the treatment time window including the minimal change of the spatial parameter in advance.

The swelling rules define how the swelling may continue based on the actually measured swelling progression, i.e. based on the actually determined changes of the spatial parameter caused by swelling. The swelling rules can be implemented as functions, tables, et cetera. They can be defined by a priori population-based statistics of a "time versus spatial parameter change" relationship.

The treatment time window determination unit can therefore be adapted to determine the treatment time window based on the actual swelling progression and/or the future swelling progression. Moreover, the treatment time window determination unit can be adapted to determine the treatment time window such that the derivative of the swelling progression within the treatment time window is smaller than a predefined threshold, which can be predefined such that a brachytherapy performed within the treatment time window provides very good therapy results as assessed by, for instance, a physician, i.e. the predefined threshold can be determined based on prior brachytherapy data obtained from a larger group of patients. The treatment time window is preferentially determined such that the dimensions of the living object are substantially not modified within the treatment time window.

In an embodiment the imaging unit is adapted to update the images of the living object during a brachytherapy procedure, wherein the planning unit is adapted to adapt the placing plan to the updated images. Thus, images of the living object can be generated during different stages of the brachytherapy procedure, for instance, during inserting catheters and after the catheters have been inserted, in particular, during the treatment stage, in which the one or several radiation sources are navigated within the one or several catheters for applying the radiation to the target region. In each of these stages the previously determined placing plan, in particular, an initial placing plan, can be modified in accordance with the actually generated images of the living object, in particular, in accordance with an actually determined treatment time window. This allows the brachytherapy apparatus to adapt the actual brachytherapy to an actually measured swelling of the living object shown in the generated images.

In particular, the imaging unit can be adapted to update the images of the living object in the treatment time window, wherein the planning unit can be adapted to adapt the placing plan to the updated images in the treatment time window. Thus, also the planning can be performed, i.e., for instance, an adaptation of an initial placing plan, can be performed during the treatment time window, in which the change of the spatial parameter like the volume of the living object caused by swelling is minimal, thereby reducing the influence of the swelling on the planning, which can lead to a further improved brachytherapy.

The imaging unit can be adapted to update the images of the living object during a brachytherapy procedure, wherein the spatial parameter determination unit can be adapted to update the spatial parameter determination based on updated images of the living object, wherein the treatment time window determination unit can be adapted to update the treatment time window depending on the updated spatial parameter and wherein the planning unit can be adapted to adapt the placing plan to the updated treatment time window. Preferentially the brachytherapy apparatus further comprises a position determination unit for determining the position of the placing unit within the living object, wherein the planning unit is further adapted to determine the placing plan depending on the determined position of the placing unit within the living object. The placing unit preferentially comprises one or several catheters, wherein the position determination unit is preferentially adapted to determine the position of the one or several catheters within the living object, i.e. the position determination unit is preferentially adapted to determine a part of the placing unit being formed by one or several catheters of the placing unit.

The position determination unit can be adapted to update the determination of the position of the placing unit within the living object at different times during a brachytherapy procedure, wherein the planning unit can be adapted to adapt the placing plan in accordance with an updated determined position of the placing unit. In particular, the position determination unit can be adapted to simultaneously track positions of several catheters of the placing unit, during and after the catheter insertion process. For instance, electromagnetic tracking or optical shape sensing tracking of individual catheters can be performed, during and after catheter implantation, wherein the placing plan can be adapted to the actually measured positions of the catheters. Moreover, realtime continuous catheter tracking using electromagnetic tracking or optical shape sensing tracking and target monitoring using live three-dimensional imaging during treatment delivery can be provided. Detected changes can be fed back to the treatment planning system, i.e. the planning unit, for potential placing plan re-optimization, creating a feedback loop for adaptive treatment planning and delivery.

In a preferred embodiment the placing unit comprises several catheters, wherein the position determination unit is adapted to determine the positions of the catheters within the living object, wherein the planning unit is adapted to determine inter-catheter spacings between catheters and to determine the placing plan depending on the determined inter-catheter spacings. In particular, the position determination unit and the planning unit can be adapted to provide a realtime continuous or intermittent estimation of inter-catheter relationships using, for instance, electromagnetic tracking or optical shape sensing tracking. Monitoring the inter-catheter spacings and using these monitored inter-catheter spacings for determining, in particular, adapting, the placing plan can further improve the quality of the brachytherapy, which is performed in accordance with the placing plan.

The planning unit can also be adapted to determine a spatial relationship between the placing unit and the living object based on the determined position of the placing unit and an image of the living object generated by the imaging unit and to determine the placing plan further depending on the determined spatial relationship between the placing unit and the living object. For instance, the position determination unit and the planning unit can be adapted to provide a realtime continuous or intermittent estimation of catheter-living object relationships using electromagnetic tracking or optical shape sensing tracking and live three-dimensional imaging like live three-dimensional ultrasound imaging. Determining the spatial relationship between the placing unit and the living object and considering this spatial relationship while determining, in particular, adapting, the placing plan can further improve the quality of the placing plan and, thus, the brachytherapy.

It is preferred that the position determination unit is adapted to perform an electromagnetic positioning technique or an optical shape sensing positioning technique. These techniques allow accurately determining the position of the placing unit, in particular, of catheters of the placing unit within the living object, thereby further improving the quality of the placing plan, which may be determined inter alia based on the position of the placing unit within the living object.

In an embodiment the planning unit is adapted to determine the target region within the living object based on a provided image of the living object and to determine the placing plan based on the determined target region. For instance, a three-dimensional image of the living object can be provided, wherein the image is preferentially a magnetic resonance image or an ultrasound image. Moreover, the planning unit can be adapted to delineate the target region within the living object, wherein a segmentation algorithm can be applied to the image for completely automatically or semi-automatically delineating the target region. The planning unit can also comprise a graphical user interface for allowing a user like a radiologist to manually delineate the target region within the living object, in order to determine the target region. In an embodiment, the planning unit is adapted to delineate a focal tumor as the target region within a prostate being the living object in this embodiment.

The provided image can be an initial image, which may show the living object before the placing unit has been inserted into the living object, in order to allow the planning unit to generate an initial placing plan based on the target region identified in the provided image. The provided image can also be an image, which has been generated during or after the insertion of the placing unit into the living object, wherein in this provided image the target region can be identified and the identified target region can be used for adapting a previous placing plan, in particular, the initial placing plan. For generating the image showing the living object before the placing unit has been inserted into the living object an imaging unit can be used, which may be different to the imaging unit providing the images during and after the insertion procedure. The image showing the living object before the insertion procedure and the one or several images showing the living object during and after the insertion procedure can also be generated by the same imaging unit. Thus, different imaging units can be used like magnetic resonance and ultrasound imaging units, or the same imaging unit can be used for generating the different images.

It is preferred that the planning unit is adapted to determine the placing plan also based on the determined spatial parameter which changes over time with the swelling of the living object. Preferably the imaging unit is adapted to update the images of the living object during a brachytherapy procedure, wherein the spatial parameter determination unit is adapted to update the spatial parameter determination based on updated images of the living object and wherein the planning unit is adapted to adapt the placing plan to the updated spatial parameter. In particular, the spatial parameter determination unit can be adapted to determine the volume and/or shape of the living object as the spatial parameter from the images generated by the imaging unit, wherein the planning unit can be adapted to adapt the placing plan to the actually determined volume and/or shape of the living object. For instance, a realtime continuous or intermittent estimation of the volume and/or shape using live three-dimensional imaging like live three-dimensional ultrasound imaging may be provided and used for adapting the placing plan. In an embodiment, the position determination unit and the imaging unit are adapted to simultaneously determine the position of the placing unit and generate images of the living object during the insertion of the placing unit, wherein the spatial parameter determination unit is adapted to determine the spatial parameter, which changes due to swelling, from the generated images and wherein the planning unit is adapted to adapt an initial placing plan, which may have been determined before the placing unit is inserted, based on the actually determined spatial parameter and the actual position of the placing unit. Thus, the position determination unit and the imaging unit can be adapted to, for example, simultaneously perform an electromagnetic tracking of individual catheters and live three-dimensional imaging of the shape and the volume of the living object by using, for instance, ultrasound during catheter implantation, wherein the initial placing plan can be adapted to the actual swelling situation. As an alternative to electromagnetic tracking also an optical shape sensing tracking can be performed, wherein individual catheters of the placing unit can be simultaneously tracked during and/or after catheter implantation.

In an embodiment the planning unit is adapted to a) provide predefined swelling rules defining an estimated future change of the spatial parameter caused by swelling based on an actual change of the spatial parameter, b) estimate a future change of the spatial parameter caused by swelling based on the predefined rules and the determined spatial parameter of the living object, and c) determine the placing plan based on the determined spatial parameter which changes over time with the swelling of the living object. For instance, an actual placing plan, which may be an initial placing plan that has been determined before the placing unit has been inserted, can be adapted based on the estimated future change, in particular, based on an estimated further volume and/or shape of the living object caused by swelling. The placing plan can therefore not only be determined based on an actual spatial parameter, but also based on an estimated future spatial parameter. For instance, an initial plan of catheter positions may be adapted during a catheter implantation process based on a measured progression of edema and on a projected progression of edema.

In a further aspect of the present invention a brachytherapy method for applying a brachytherapy to a living object is presented, wherein the brachytherapy method comprises:
generating images of the living object over time by an imaging unit,
inserting a placing unit into the living object, wherein the living object swells when the placing unit is inserted into the living object, placing a radiation source emitting radiation close to a target region of the living object by the placing unit for directing the emitted radiation to the target region, determining a spatial parameter of the living object, which changes over time with the swelling of the living object, from the generated images of the living object by a spatial parameter determination unit, determining a treatment time window, in which a change of the spatial parameter of the living object is minimal, by a treatment time window determination unit, determining a placing plan defining placing positions within the living object at which the radiation source is to be placed and placing times defining when and how long the radiation source is to be placed at the respective placing position based on the generated images and the determined treatment time window by a planning unit, wherein the planning unit determines the placing plan such that the placing times are within the treatment time window, placing the radiation source in accordance with the determined placing plan by using the placing unit.

In a further aspect of the present invention a computer program for applying a brachytherapy to a living object is presented, wherein the computer program comprises program code means for causing a brachytherapy apparatus as defined in claim 1 to carry out the steps of the brachytherapy method as defined in claim 14, when the computer program is run on a computer controlling the brachytherapy apparatus.

It shall be understood that the brachytherapy apparatus of claim 1, the brachytherapy method of claim 14, and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
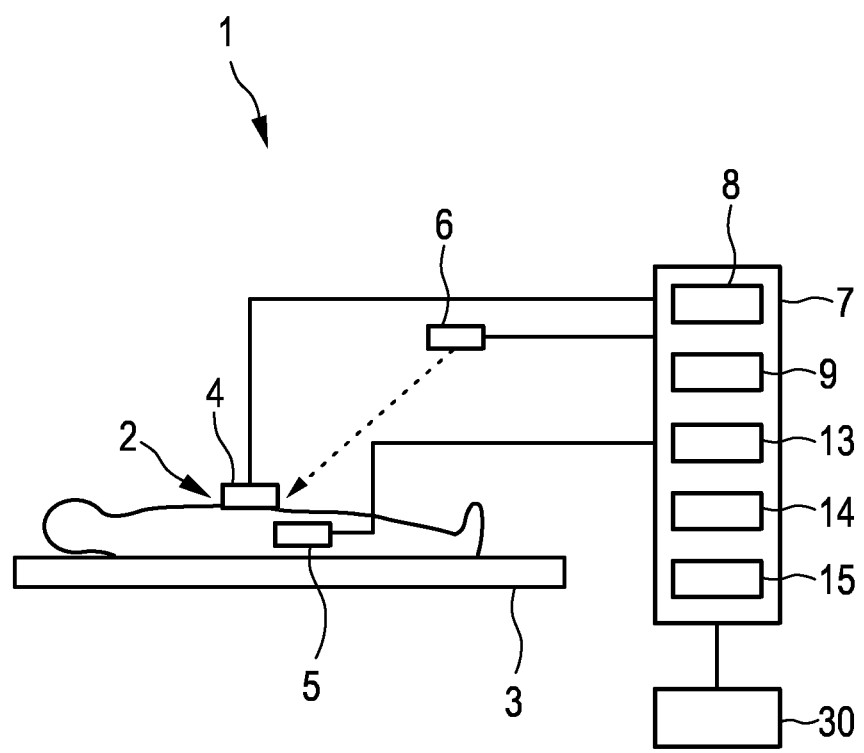
FIG. 1 shows schematically and exemplarily an embodiment of a brachytherapy apparatus for applying a brachytherapy to a living object.
Figure 2:
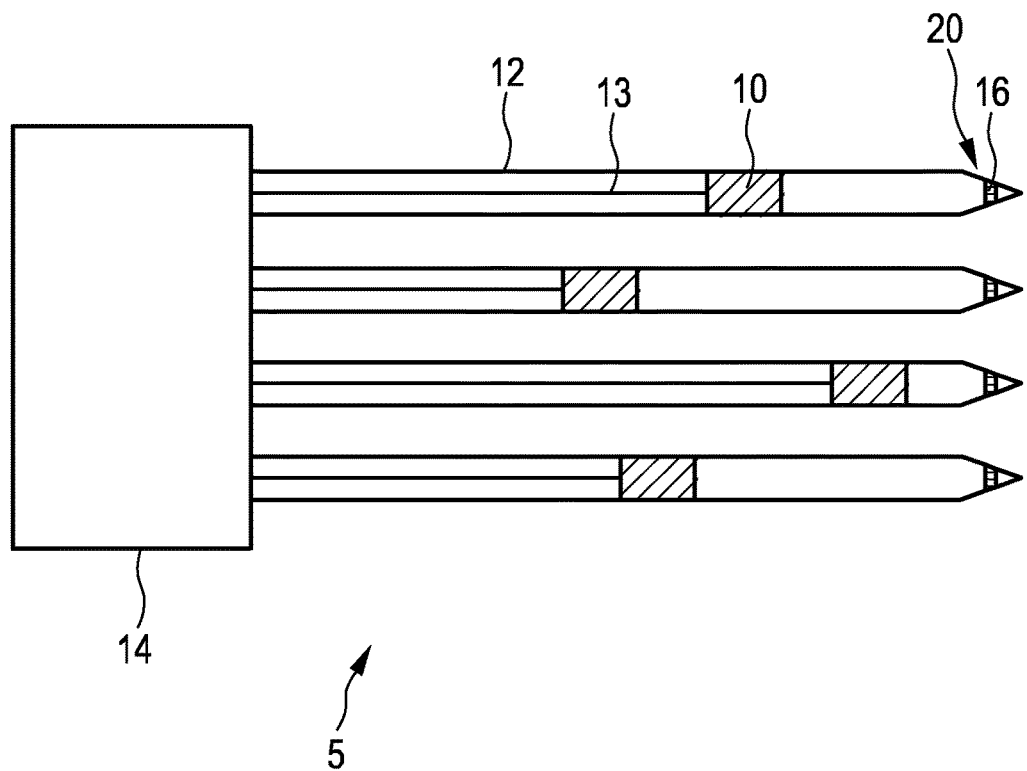
FIG. 2 shows schematically and exemplarily an embodiment of a placing unit of the brachytherapy apparatus.

FIG. 1 shows schematically and exemplarily an embodiment of a brachytherapy apparatus for applying a brachytherapy to a living object. The brachytherapy apparatus 1 comprises a placing unit 5 for being inserted into a living object of a person 2 lying on a table 3. The placing unit 5 is adapted to be inserted into the living object and to place radiation sources close to a target region of the living object for directing radiation emitted by the radiation sources to the target region. The placing unit 5 is exemplarily and schematically shown in more detail in FIG. 2.

The placing unit 5 comprises several catheters 12 with catheter tips 20 for being inserted into the living object 11. The placing unit 5 further comprises several navigation elements 13 being wires to which the radiation sources 10 are attached, wherein a respective wire 13 can be moved within a respective catheter 12 for placing a respective radiation source 10 at a desired placing position. The catheters 12 with the wires 13 are attached to a motor unit 14 comprising several motors for moving the wires 13 in a forward direction and in a backward direction for placing the radiation sources 10 at the desired placing positions. The radiation sources 10 are preferentially a radioactive radiation source emitting radioactive radiation like Ir-192.

The placing unit can comprise further elements for assisting in placing the radiation sources at the desired placing positions within the living object. For instance, the placing unit can comprise a template, which can be used for inserting the catheters in a more uniform configuration into the living object.

Figure 3:
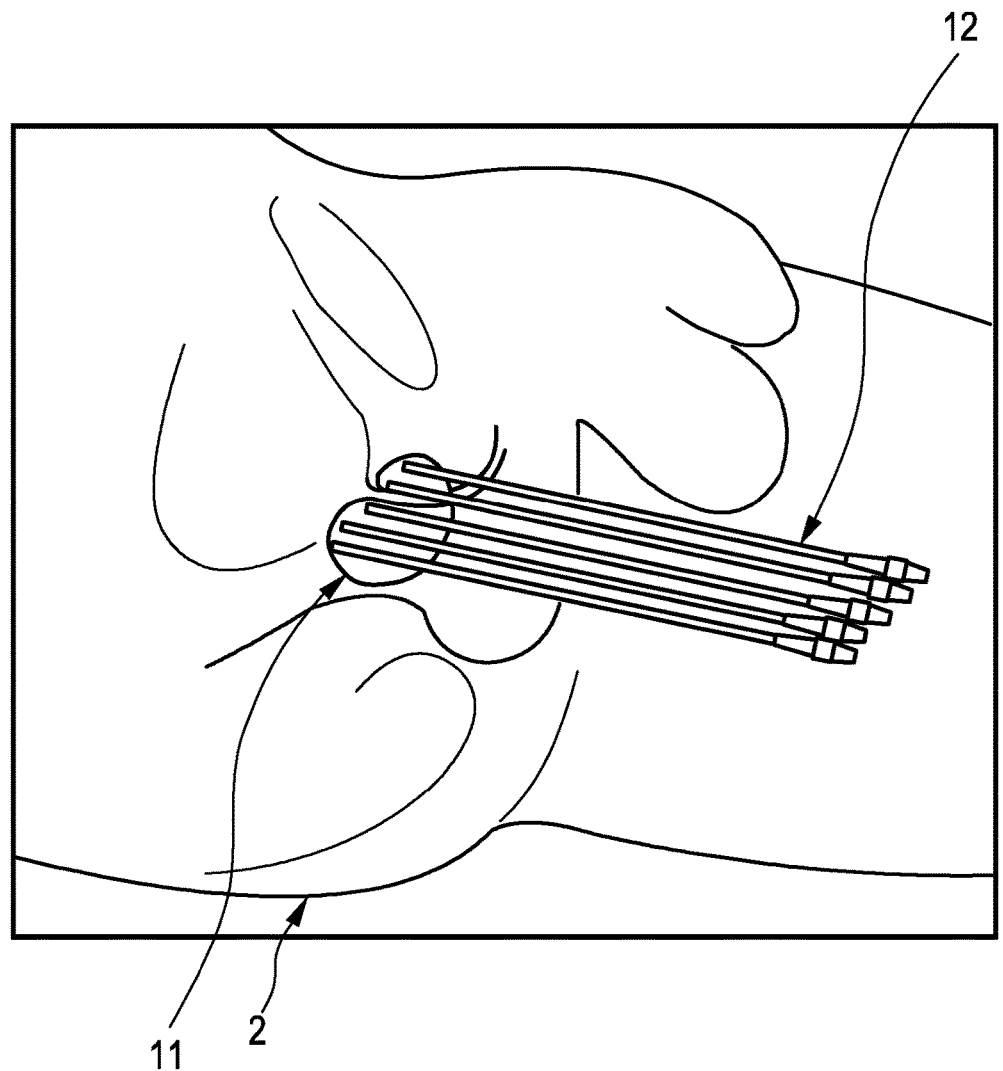
FIG. 3 shows schematically and exemplarily how catheters of the placing unit can be arranged within a prostate.

The living object 11 is preferentially a part of a person or of an animal like an organ. In this embodiment the living object 11 is a prostate. The target region is preferentially a tumor region of the part of the person or of the animal. In order to place the radiation sources close to the target region, they can be placed adjacent to or within the target region. FIG. 3 shows schematically and exemplarily a possible arrangement of the catheters 12 of the placing unit 5 within the prostate 11.

If the catheters 12 are inserted into the prostate 11 the prostate swells, i.e. an edema is progressing, which can be monitored by an imaging unit 4, 8 for generating images of the prostate 11 over time. In this embodiment the imaging unit 4, 8 is an ultrasound unit comprising one or several ultrasound transducers controlled by an ultrasound control unit 8 located in a processing and control device 7. The imaging unit 4, 8 is adapted to generate a three-dimensional image of the prostate 11. In other embodiments, the imaging unit can also be adapted to generate a two-dimensional image. Moreover, the imaging unit can also be adapted to generate another kind of image like a magnetic resonance image.

The brachytherapy apparatus 1 further comprises a spatial parameter determination unit 9 for determining a spatial parameter of the prostate 11, which changes over time with the swelling of the prostate 11, from the generated images of the prostate 11. Moreover, the brachytherapy apparatus 1 comprises a treatment time window determination unit 13 for determining a treatment time window, in which a change of the spatial parameter of the prostate 11 is minimal, and a planning unit 14 for determining a placing plan defining placing positions at which the radiation sources 10 are to be placed and placing times defining when and how long the respective radiation source 10 is to be placed at the respective placing position based on the generated images and the determined treatment time window, wherein the planning unit 14 is adapted to determine the placing plan such that the placing times are within the treatment time window. Thus, the placing unit 5 is adapted to place the several radiation sources 10 at different placing positions within the prostate 11 for performing the brachytherapy, wherein the planning unit 14 is adapted to plan the different placing positions and corresponding placing times defining when and how long the respective radiation source 10 dwells at the respective placing position.

In this embodiment the spatial parameter is the volume of the prostate 11, wherein the treatment time window determination unit 13 is adapted to determine the treatment time window such that it contains a minimum of a volume change. In particular, the treatment time window determination unit 13 can be adapted such that the volume of the prostate 11 does substantially not change in the treatment time window.

Figure 4:
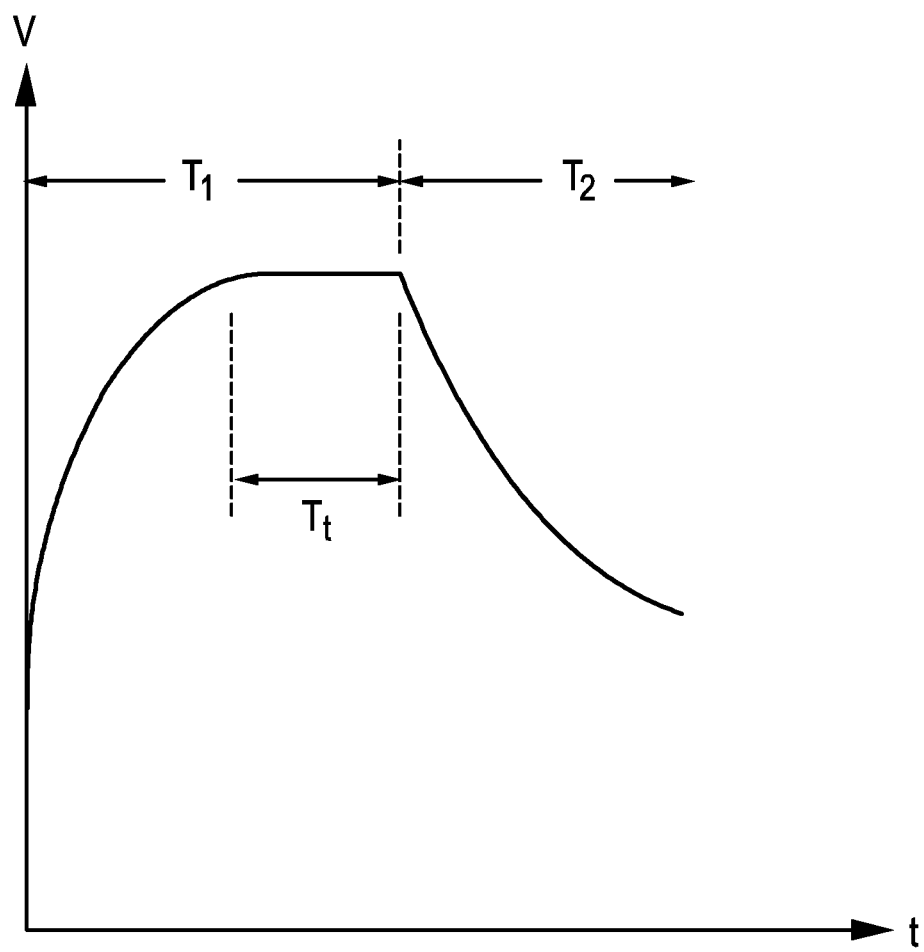
FIG. 4 illustrates exemplarily a volume change of the prostate after the catheters have been inserted into the prostate.

FIG. 4 shows schematically and exemplarily the volume V of the prostate 11 depending on the time t since final catheter implantation. As can be seen in FIG. 4, the volume V of the prostate 11 increases with time t in a first period $T_1$, until the volume V reaches a saturation value. After the saturation value has been reached, the volume V of the prostate 11 remains substantially constant in a time period $T_t$. The time period $T_1$ is in the range of some minutes or hours at the day of implanting the catheters into the prostate 11. In the time period $T_2$, which covers about 30 days, the volume V of the prostate 11 substantially exponentially decreases. The treatment time window determination unit 13 is preferentially adapted to determine the time period $T_t$ as the treatment time window, in which the treatment of the prostate 11 should be performed.

The spatial parameter can also be a spatial parameter of only a part of the living object, in particular, of the target region being, in this embodiment, a tumor region of the prostate. Moreover, the spatial parameter can also be another spatial parameter not being the volume like the shape of the living object, in particular, of a part of the living object such as the shape of a tumor region of the living object. Also several spatial parameters can be determined and used for determining the treatment time window. For instance, several spatial parameters can be determined for describing an anisotropic volume change, i.e. a combined volume and shape change, wherein based on these spatial parameters the treatment time window can be determined. The spatial parameters can define, for instance, positions of different elements of the living object, wherein these positions of the different elements form a representation of the living object that changes over time and can thereby define an anisotropic volume change.

The brachytherapy apparatus 1 further comprises a control unit 15 for controlling the placing unit 5 depending on the determined placing plan. Alternatively, the placing unit 5 may be used manually in accordance with the determined placing plan, wherein a user may move the radiation sources 10 via the wires 13 within the catheters 12 in accordance with the determined placing plan.

The treatment time window determination unit 13 is adapted to provide predefined swelling rules defining an estimated future change of the spatial parameter caused by swelling based on an actual change of the spatial parameter, to estimate a future change of the spatial parameter caused by swelling based on the predefined rules and the determined spatial parameter of the prostate 11, and to determine the treatment time window based on the estimated future change of the spatial parameter. In particular, the swelling rules can define how the volume of the prostate 11 will change depending on an actually measured volume change of the prostate 11. Thus, the swelling rules preferentially define how the swelling likely continues based on the actually measured swelling progression. The swelling rules can be implemented as functions, tables, et cetera. They can be defined by a priori population-based statistics of a "time versus spatial parameter change" relationship.

For instance, a database can be provided, which comprises spatial parameter changes measured at multiple persons, after the placing unit has been inserted into the persons. The measurement results directly or derived parameters derived from the measurement results can be used as the swelling rules. For instance, it can be determined which measurement result stored in the database provides the best match with an actually measured spatial parameter, which changes over time. It can then be assumed that the further change of the best matching measurement result stored in the database corresponds to the future change of the actually measured spatial parameter.

The treatment time window determination 13 is therefore adapted to determine the treatment time window based on the future swelling progression. Moreover, the treatment time window determination unit 13 is adapted to determine the treatment time window such that the derivative of the swelling progression within the treatment time window, i.e. the derivative of the volume change of the prostate caused by swelling within the treatment time window, is smaller than a predefined threshold, which can be predefined such that a brachytherapy performed within the treatment time window provides very good therapy results as assessed by, for instance, a physician, i.e. the predefined threshold can be determined based on a priori brachytherapy data obtained from a larger group of patients. Preferentially, the treatment time window determination unit 13 is adapted to determine the treatment time window such that the volume of the prostate 11 does substantially not change within the treatment time window.

The brachytherapy apparatus 1 further comprises a position determination unit 6, 16 for determining the position of the placing unit 5 within the prostate 11, wherein the planning unit 14 is adapted to determine the placing plan also depending on the determined position of the placing unit 5 within the prostate 11. In this embodiment the position determination unit 6, 16 is adapted to determine the position of the catheters 12 within the prostate 11, wherein the planning unit 14 is adapted to determine the placing plan also depending on the determined positions of the catheters 12 within the prostate 11.

The position determination unit preferentially comprises an electromagnetic sensing unit 6, which cooperates with an electromagnetic sensing element 16 arranged within the tip 20 of the respective catheter 12 for determining the position of the respective catheter 12 within the prostate 11. In another embodiment, the electromagnetic sensing element can also be translated throughout the length of the respective catheter, in order to determine the three-dimensional shape and pose of the respective catheter. Alternatively, the position determination unit can be adapted to determine the position of the catheters 12 within the prostate 11 by optical shape sensing. In this case each catheter 12 comprises an optical shape sensing fiber connected to an optical shape sensing unit for determining the position of the respective catheter by optical shape sensing. Also in this case the three-dimensional shape and pose of the respective catheter can be determined.

In this embodiment the planning unit 14 is adapted to determine inter-catheter spacings between neighboring catheters 12 based on the determined positions of the catheters 12 and to determine the placing plan depending on the determined inter-catheter spacings. Moreover, the planning unit 14 is adapted to determine a spatial relationship between the catheters 12 and the prostate 11 based on the determined position of the catheters 12 and based on an image of the prostate 11 generated by the imaging unit 5, 8 and to determine the placing plan further depending on the determined spatial relationship between the catheters 12 and the prostate 11. For example, the planning unit 14 can be adapted to determine the position of each catheter 12 relative to the prostate 11 and to use these determined positions for generating the placing plan, in particular, for adapting a previously generated placing plan to the actually measured relative positions of the catheters 12 within the prostate 11.

The planning unit 14 is also adapted to determine the target region, which is preferentially a tumor region, within the prostate 11 based on a provided image of the prostate 11 and to determine the placing plan also based on the determined target region. For instance, a three-dimensional image of the prostate can be provided, wherein the image is preferentially a magnetic resonance image or an ultrasound image. Moreover, the planning unit 14 can be adapted to delineate the target region within the prostate 11, wherein a segmentation algorithm can be applied to the image for completely automatically or semi-automatically delineating the target region. The planning unit 14 can also comprise a graphical user interface for allowing a user like a radiologist to manually delineate the target region within the prostate 11, in order to determine the target region. In an embodiment the planning unit is adapted to delineate a focal tumor as the target region within the prostate 11.

The planning unit 14 is further adapted to determine the placing plan based on the determined spatial parameter being, in this embodiment, the volume and additionally of the prostate 11, which changes over time with the swelling of the prostate 11. The planning unit 14 can be adapted to determine the placing plan based on an actually measured volume of the prostate 11 and based on an estimated future change of the volume of the prostate 11, which can be determined by applying the swelling rules to a measured actual change of the volume of the prostate. Thus, an actual placing plan, which may be an initial placing plan that has been determined before the catheters 12 have been inserted into the prostate 11, can be adapted based on the estimated future change, in particular, an estimated future volume of the prostate. The placing plan can therefore not only be determined based on an actual volume, but also based on an estimated future volume. An initial plan of catheter positions can therefore be adapted during a catheter implantation process based on a measured progression of edema and on a projected progression of edema.

The imaging unit 4, 8 and the position determination unit 6, 16 are preferentially adapted to generate images of the prostate 11 and to determine the positions of the catheters 12 within the prostate 11 during one or several stages of the brachytherapy, in order to monitor the swelling of the prostate 11 and in order to adapt the placing plan in accordance with the monitored swelling. In particular, the brachytherapy apparatus 1 is preferentially adapted to generate images of the prostate 11 and to determine the positions of the catheters 12 within the prostate 11 during the insertion of the catheters 12 into the prostate 11 and after the catheters 12 have been inserted into the prostate 11, in particular, during the treatment of the target region by using the radiation sources 10, wherein during these different stages of the brachytherapy the placing plan can be adjusted in accordance with the actually generated images of the prostate and the actually determined positions of the catheters within the prostate. For instance, the imaging unit 4, 8 can update the images of the prostate 11 during a brachytherapy procedure, wherein the planning unit 14 can be adapted to adapt the placing plan to the updated images. In particular, the spatial parameter determination unit 9 can be adapted to update the spatial parameter determination based on the updated images of the prostate 11, wherein the treatment time window determination unit 13 can be adapted to update the treatment time window depending on the updated spatial parameter and wherein the planning unit 14 can be adapted to adapt the placing plan to the updated treatment time window such that the placing times are within the updated treatment time window. Moreover, based on the actually measured positions of the catheters 12 within the prostate 11, i.e. based on the updated positions of the catheters 12 within the prostate 11, updated inter-catheter spacings between neighboring catheters 12 can be determined and based on the updated images and the updated positions of the catheters 12 within the prostate 11 updated spatial relationships between the catheters 12 and the prostate 11 can be determined, wherein this updated information together with an updated volume of the prostate 11 and an updated target region within the prostate 11 can be used by the planning unit 14 for adapting the placing plan to the actually determined, updated information. The images of the prostate 11 and the positions of the catheters 12 within the prostate 11 can be provided in realtime continuously or intermittently for updating at least one of the volume of the prostate 11, the spatial relationship between the catheters 12 and the prostate 11, the inter-catheter spacings, the treatment time window and the target region, wherein the planning unit 14 is adapted to adapt the placing plan to the updated information, thereby providing a feedback loop for adaptive treatment planning and delivery.

Figure 5:
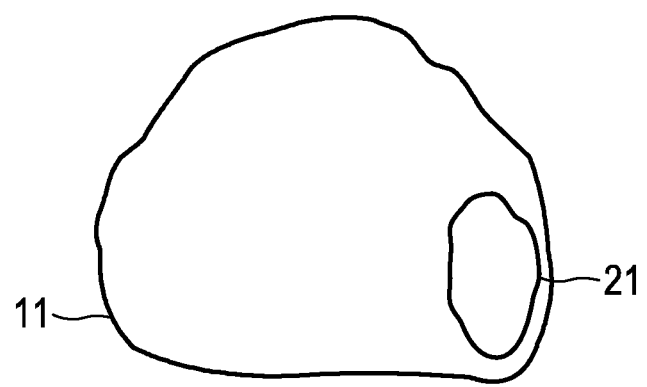
FIG. 5 shows schematically and exemplarily the prostate before the insertion of the catheters.
Figure 6:
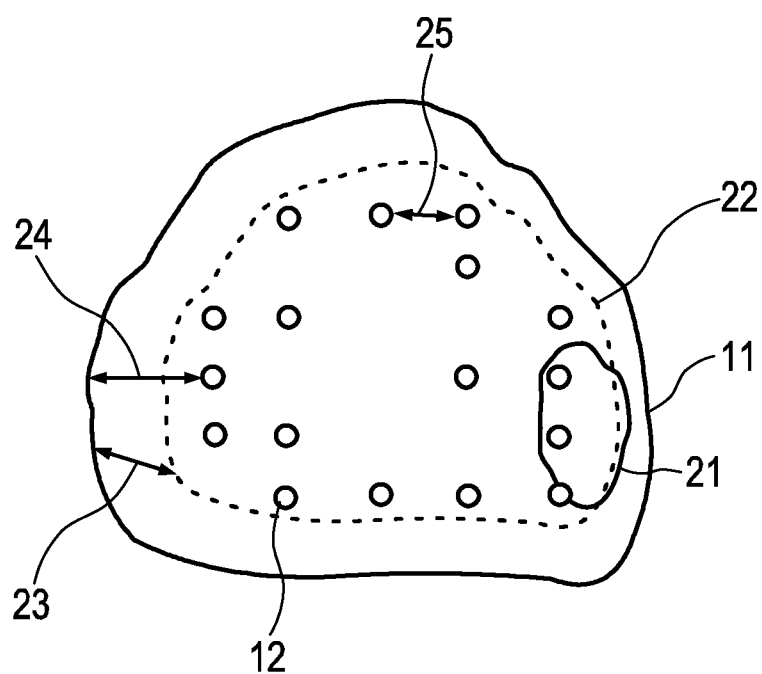
FIG. 6 shows schematically and exemplarily the prostate after the catheters have been inserted.

FIGS. 5 and 6 illustrate the different parameters used for determining the placing plan before insertion of the catheters 12, during insertion and after the insertion has been completed. In particular, FIG. 5 shows schematically and exemplarily the prostate 11 with a prostatic tumor 21 prior to catheter implantation. The prosthetic tumor 21 defines the target region. An image like a magnetic resonance image, an ultrasound image or an image of another imaging modality can be provided to the planning unit 14 for allowing the planning unit 14 to determine the dimensions of the prostate 11 and of the target region 21 prior to catheter implantation by using, for instance, known segmentation algorithms. The planning unit 14 is preferentially further adapted to determine an initial placing plan depending on the dimensions of the prostate 11 and the target region 21 within the prostate 11 prior to catheter implantation.

During and after catheter implantation the prostate 11 swells as indicated in FIG. 6. FIG. 6 shows the swelling prostate 11 having a volume being larger than the volume of the initial prostate, which is indicated in FIG. 6 by the broken line 22. In FIG. 6, the double arrow 23 indicates the volume change of the prostate 11 due to swelling, the double arrow 24 indicates the spatial relation between the catheters 12 and the prostate 11, which is, for instance, a distance of the respective catheter 12 to an outer surface of the prostate 11, and the double arrow 25 indicates an inter-catheter spacing between neighboring catheters 12.

In this embodiment, the respective catheter-prostate relationship indicated by the double arrow 24 is defined as the shortest distance of the tip of the respective catheter to the outer surface of the prostate. However, in another embodiment the catheter-prostate relationship can also be defined by another metric. For instance, the distance from one or more given catheters to one or more anatomical points of interest of the prostate can also be initially quantified and tracked over time. The one or more anatomical points of interest can be delineated in the generated image, for instance, in a generated ultrasound image, a generated magnetic resonance image or an image generated by another imaging modality. The volume change indicated by the double arrow 23 can be quantified by calculating the derivative of the volume, by calculating differences from multiple volumes acquired over time, et cetera. The inter-catheter spacing indicated by the double arrow 25 can be a spacing between closest neighbors. However, it can also be defined as a spacing between any two catheters.

Besides the placing times, i.e. the dwell times, and the placing positions, i.e. the dwell positions, the placing plan can specify the number of catheters, the position and angle of each catheter in the living object, the skin entry points, et cetera. The placing plan is preferentially determined such that the target region of the living object receives a radiation dose being equal to or larger than a given predefined radiation dose value and such that given predefined dosimetric constraints for the person, in particular, for the living object and preferentially further neighboring parts of the person are satisfied. If dosimetric constraints are considered also for the neighboring parts of the person, the generated image preferentially also shows these parts and the spatial relation of these neighboring parts to the living object, in particular, to the target region, to be treated is preferentially considered while determining the placing plan. Examples of dosimetric constraints are a V100 value, which defines the volume receiving a dose of 100 Gy, and a D20 value, which defines the dose received by 20 percent of the volume. The planning unit can be adapted to use an optimization algorithm for determining the placing plan such that dwell positions and dwell times are optimized, in order to generate a three-dimensional dose map, according to which the target region receives a given predefined radiation dose and according to which the dosimetric constraints are satisfied. The planning unit can be adapted to use the AAPM TG-43 formalism for performing the dose calculation or to use another optimization algorithm.

The brachytherapy apparatus further comprises a display unit 30 for showing, for instance, the generated images and determined catheter positions to a user like a physician.

Figure 7:
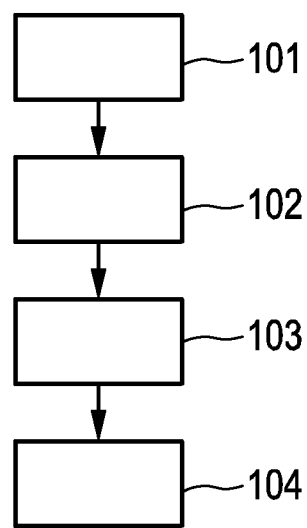
FIG. 7 shows a flowchart exemplarily illustrating an embodiment of a brachytherapy method for applying a brachytherapy to a living object.

In the following an embodiment of a brachytherapy method for applying a brachytherapy to a living object will exemplarily be described with reference to a flowchart shown in FIG. 7.

In step 101 an initial image of the prostate like a magnetic resonance image or an ultrasound image is provided to the planning unit for allowing the planning unit to determine the position of the prostate within the person and to determine the position of a tumor region being a target region within the prostate. The planning unit then determines an initial placing plan defining how long radiation sources should be placed at which positions within the prostate for treating the target region.

In step 102 the catheters of the placing unit are inserted into the person, in particular, into the prostate, in accordance with the initial placing plan. During the insertion procedure the prostate swells and the imaging unit generates images of the swelling prostate and the position determination unit determines the positions of the catheters within the prostate. Moreover, based on the generated images of the prostate and the determined positions of the catheters the planning unit adapts the initial placing plan, in order to account for the progressing edema. In particular, updated inter-catheter spacings, an updated volume of the prostate, an updated position of the target region, an updated spatial relationship between the prostate and the catheters, and a treatment time window can be determined and used for adapting the placing plan. Also after the insertion of the catheters has been completed, in step 103 the swelling of the prostate can further be monitored by generating further images of the prostate and by further determining the positions of the catheters within the prostate, wherein also in this stage of the brachytherapy after the insertion of the catheters the placing plan can be adapted to updated parameters, which are updated in accordance with the actually generated images and the actually determined positions of the catheters within the prostate. In step 104 the radiation sources are arranged within the inserted catheters at different placing positions for respective placing times within the determined treatment time window in accordance with the adapted placing plan, in order to treat the target region. Also during this treatment stage of the brachytherapy the imaging unit may generate images of the prostate and the position determination unit may determine the positions of the catheters, wherein this actually measured information can be used for determining updated parameters like updated inter-catheter spacings, an updated volume of the prostate, et cetera, which can be used for further adapting the placing plan, wherein the placing of the radiation sources within the prostate can be performed in accordance with the adapted placing plan.

The brachytherapy apparatus is preferentially adapted to perform a high dose rate (HDR) brachytherapy as a form of cancer therapy that utilizes high doses of ionizing radiation delivered over a short period of time in the order of some minutes directly at or near the target. Due to the high dose rate delivery rates involved the margin of error should be minimal. Hence, the brachytherapy apparatus is adapted to develop an accurate treatment plan, i.e. a placing plan, and to deliver radiation according to the developed treatment plan. After the catheters have been inserted into the prostate in accordance with an initial placing plan, the actual real positions of the catheters are determined and used for updating the placing plan, in particular, for updating the placing positions and placing times of the radiation sources within the respective catheter. Also after the placing positions and placing times have been adapted to the actual, real positions of the catheters inserted into the prostate, the positions of the catheters are preferentially further tracked, in order to account for a motion of the target region relative to the catheters. This tracking may be performed after the catheters have been inserted and before treatment delivery and also during treatment delivery.

Although in an above described embodiment shown in FIG. 3 the arrangement of catheters is implanted transperineally in the prostate, in other embodiments the arrangement of catheters can also be implanted differently into the prostate. Moreover, in other embodiments the catheters may not be implanted in the prostate, but in another living object like another organ for treating the organ, in particular, for destroying a tumor in the organ.

Although in an above described embodiment the ultrasound unit is adapted to be placed on the outer skin of the person for generating the ultrasound images, in other embodiments the imaging unit can also be another kind of ultrasound imaging unit. For example, the imaging unit can comprise a trans-rectal ultrasound probe for generating the ultrasound images. The imaging unit can also be another imaging modality like a magnetic resonance imaging modality.

Generally, inconsistencies between treatment planning and delivery may result due to various reasons, examples of which are motion of the target, for instance, due to breathing, other physiological processes, person movement, motion of the catheters, et cetera. Another potential change that could happen between treatment planning and delivery is the change in shape and volume of the target, i.e. of the living object to be treated, due to edema, i.e. swelling, resulting from the multi-catheter insertion. This swelling is a natural reaction of the tissue to the introduction of foreign objects. Edema of the living object can result in changes to relative spatial relationships between the catheters and the living object, in particular, between the catheters and the target region. These changes can generally result in an invalidation of an originally developed treatment plan, i.e. of an original placing plan.

The brachytherapy apparatus is therefore preferentially adapted to use a combination of electromagnetic tracking, or optical shape sensing tracking, and three-dimensional imaging, in particular, three-dimensional ultrasound imaging, at intermittent time intervals between an initial treatment planning and delivery, and optionally also in realtime during treatment delivery. This allows the brachytherapy apparatus to provide a time-dependent characterization of the developing edema in the time between the initial planning and the delivery and optionally also during delivery. This ability to gather accurate knowledge of the varying target shape and volume enables intelligent and adaptive treatment planning, which may lead to a higher confidence in treatment delivery.

The brachytherapy apparatus preferentially uses the following technologies to realize the goal of intelligent and adaptive treatment planning and delivery: two-dimensional or three-dimensional ultrasound imaging, alternatively or in addition, three-dimensional magnetic resonance imaging, and electromagnetic tracking, alternatively or in addition, optical shape sensing tracking. These imaging and tracking technologies can be utilized individually and together to determine a) focal cancerous regions that may require dose boosting, in particular, by using magnetic resonance imaging, b) realtime adaptations in catheter placement based on measured edema progression and projected edema progression, in particular, based on patient-specific measurements and a priori population statistics, c) target shape and volume changes by using, for instance, live three-dimensional ultrasound imaging, wherein shape and volume changes of the living object and, in particular, of the target region are determined, d) inter-catheter distance relationships, especially by using electromagnetic tracking or optical shape sensing tracking, and e) catheter-living object distance relationships, in particular, catheter-target region distance relationships, preferentially by using electromagnetic tracking or optical shape sensing tracking and live three-dimensional ultrasound imaging.

The brachytherapy apparatus is preferentially adapted to determine an optimal time window, i.e. the treatment time window, to perform treatment planning and delivery based on a stabilization of the volume of the living object depending on an evaluation of the developing edema. The brachytherapy apparatus provides therefore an intelligent treatment planning. Generally, after one day the progression of edema subsequent to implanting the catheters has an exponential fall off, wherein the prostate is generally 30 to 100 percent larger on the day after the implantation of the catheters compared to its size prior to implantation. The swelling may be reduced to a size of being about 10 percent larger than the initial volume about a month after the implantation. However, the progression of edema on the day of the implant, in particular, on a time scale of minutes and hours is generally not known. The workflow performed by using the brachytherapy apparatus is therefore adapted to provide valuable information on the progression of edema in HDR procedures and also allows for a patient-specific determination of the timing of HDR treatment planning and delivery.

The image, which is provided for performing the initial planning of the placing plan before inserting the catheters and which is preferentially a magnetic resonance image, can be utilized to incorporate focal dose boosting in the initial placing plan, i.e. in the original treatment plan. Further, three-dimensional image fusion between the provided prior image, which is preferentially a magnetic resonance image, and a realtime three-dimensional ultrasound image, which may be generated during and after insertion of the catheters, can be performed. The prior image can then also be used to delineate one or several cancerous regions, i.e. one or several target regions, wherein the resulting spatial information about the one or several target regions within the living object can be used to further improve the adaptation of the placing plan to the actual spatial situation. The three-dimensional image fusion can therefore be utilized along with real time continuous catheter tracking, in particular during treatment delivery, to enable adaptive and efficient delivery of focal dose boosts.

The tissue edema resulting from the multi-catheter implantation results in a swelling of the living object. This causes changes in the spatial relationships between the individual catheters and also between the catheters and the living object, in particular, between the catheters and the target region. In case of focal dose boosting the catheters that were originally intended to provide the dose boost in the original treatment plan, i.e. in the initial placing plan, may no longer be the appropriate catheters to provide the dose boost, because their relative positions may have changed. Hence, a continuous tracking of one or more catheters near the target region needing a dose boost is helpful in such cases. Also a distributed sensing of all catheter channels may be helpful. All these modifications from the original treatment plan can be tracked and accounted for using the technologies and workflow described above.

The brachytherapy apparatus is preferentially adapted to use electromagnetic tracking or optical shape sensing tracking and realtime imaging in a combined way to track and account for catheter-induced edema of target tissue. The placing plan can be determined such that by applying the radiation dose in accordance with the placing plan dosimetric hot or cold spots are created in the living object, a heterogeneous target dosage is applied, dose boosting is performed and/or a focal treatment is performed.

The brachytherapy apparatus can be adapted to provide an adaptive synchronization of treatment planning and delivery for, for instance, dose boosting or focal treatments, i.e. to adapt the placing plan and tailor the delivery to the adapted plan such that, for instance, dose boosting or focal treatment procedures are performed.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the target region within the living object, the determination of the spatial parameter over time, the determination of the inter-catheter spacings, the determination of the treatment time window, et cetera performed by the planning unit can be performed by any other number of units or devices. The determinations and/or the control of the brachytherapy apparatus in accordance with the brachytherapy method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a brachytherapy apparatus for applying a brachytherapy to a living object. The brachytherapy apparatus comprises a planning unit for determining a placing plan defining placing positions and placing times for one or several radiation sources within the living object and close to a target region. The placing plan is determined such that the placing times are within a treatment time window determined by a treatment time window determination unit, wherein within the treatment time window a change of a spatial parameter of the living object caused by swelling is minimized. An adverse influence on the brachytherapy due to swelling can thereby be minimized, which improves the quality of the brachytherapy.

The invention claimed is:

1. A brachytherapy apparatus for applying a brachytherapy to a living object, the brachytherapy apparatus comprising:
a radiation source emitting radiation,
a placing unit for being inserted into the living object and for placing the radiation source close to a target region of the living object for directing the emitted radiation to the target region, wherein the living object swells when the placing unit is inserted into the living object,
an imaging unit for generating images of the living object over time,
a spatial parameter determination unit for determining a spatial parameter of the living object, which changes over time with the swelling of the living object, from the generated images of the living object,
a treatment time window determination unit for determining a treatment time window, in which a change of the spatial parameter of the living object is minimal,
a planning unit for determining a placing plan defining placing positions within the living object at which the radiation source is to be placed and placing times defining when and how long the radiation source is to be placed at the respective placing position based on the generated images and the determined treatment time window, wherein the planning unit is adapted to determine the placing plan such that the placing times are within the treatment time window.

2. The brachytherapy apparatus as defined in claim 1, wherein the treatment time window determination unit is adapted to:
provide predefined swelling rules defining at least one estimated future change of the spatial parameter caused by swelling based on an actual change of the spatial parameter,
estimate a future change of the spatial parameter caused by swelling based on the predefined rules defining at least one estimated future change of the spatial parameter caused by swelling based on an actual change of the spatial parameter and the determined spatial parameter of the living object,
determine the treatment time window based on the estimated future change of the spatial parameter.

3. The brachytherapy apparatus as defined in claim 1, wherein the imaging unit is adapted to update the images of the living object during a brachytherapy procedure, wherein the planning unit is adapted to adapt the placing plan to the updated images.

4. The brachytherapy apparatus as defined in claim 3, wherein the imaging unit is adapted to update the images of the living object in the treatment time window, wherein the planning unit is adapted to adapt the placing plan to the updated images in the treatment time window.

5. The brachytherapy apparatus as defined in claim 1, wherein the imaging unit is adapted to update the images of the living object during a brachytherapy procedure, wherein the spatial parameter determination unit is adapted to update the spatial parameter determination based on updated images of the living object, wherein the treatment time window determination unit is adapted to update the treatment time window depending on the updated spatial parameter and wherein the planning unit is adapted to adapt the placing plan to the updated treatment time window.

6. The brachytherapy apparatus as defined in claim 1, wherein the brachytherapy apparatus further comprises a position determination unit for determining a position of the placing unit within the living object, wherein the planning unit is further adapted to determine the placing plan depending on the determined position of the placing unit within the living object.

7. The brachytherapy apparatus as defined in claim 6, wherein the position determination unit is adapted to update the determination of the position of the placing unit within the living object at different times during a brachytherapy procedure, wherein the planning unit is adapted to adapt the placing plan in accordance with an updated determined position of the placing unit.

8. The brachytherapy apparatus as defined in claim 6, wherein the placing unit comprises several catheters, wherein the position determination unit is adapted to determine positions of the catheters within the living object, wherein the planning unit is adapted to determine inter-catheter spacings between catheters and to determine the placing plan depending on the determined inter-catheter spacings.

9. The brachytherapy apparatus as defined in claim 6, wherein the planning unit is adapted to determine a spatial relationship between the placing unit and the living object based on the determined position of the placing unit and an image of the living object generated by the imaging unit and to determine the placing plan further depending on the determined spatial relationship between the placing unit and the living object.

10. The brachytherapy apparatus as defined in claim 1, wherein the planning unit is adapted to determine the target region within the living object based on a provided image of the living object and to determine the placing plan based on the determined target region.

11. The brachytherapy apparatus as defined in claim 1, wherein the planning unit is adapted to determine the placing plan based on the determined spatial parameter which changes over time with the swelling of the living object.

12. The brachytherapy apparatus as defined in claim 11, wherein the imaging unit is adapted to update the images of the living object during a brachytherapy procedure, wherein the spatial parameter determination unit is adapted to update the spatial parameter determination based on updated images of the living object and wherein the planning unit is adapted to adapt the placing plan to the updated spatial parameter.

13. The brachytherapy apparatus as defined in claim 11, wherein the planning unit is adapted to:
provide predefined swelling rules defining an estimated future change of the spatial parameter caused by swelling based on an actual change of the spatial parameter,
estimate a future change of the spatial parameter caused by swelling based on the predefined rules and the determined spatial parameter of the living object,
determine the placing plan based on the determined spatial parameter which changes over time with the swelling of the living object.

14. A brachytherapy method for applying a brachytherapy to a living object, the brachytherapy method comprising:
generating images of the living object over time by an imaging unit,
inserting a placing unit into the living object, wherein the living object swells when the placing unit is inserted into the living object,
placing a radiation source emitting radiation close to a target region of the living object by the placing unit for directing the emitted radiation to the target region,
determining a spatial parameter of the living object, which changes over time with the swelling of the living object, from the generated images of the living object by a spatial parameter determination unit,
determining a treatment time window, in which a change of the spatial parameter of the living object is minimal, by a treatment time window determination unit,
determining a placing plan defining placing positions within the living object at which the radiation source is to be placed and placing times defining when and how long the radiation source is to be placed at the respective placing position based on the generated images and the determined treatment time window by a planning unit, wherein the planning unit determines the placing plan such that the placing times are within the treatment time window,
placing the radiation source in accordance with the determined placing plan by using the placing unit.

15. A brachytherapy apparatus for applying a brachytherapy to a living object, the brachytherapy apparatus comprising:
a radiation source emitting radiation,
a placing unit comprising at least one catheter for being inserted into the living object and for placing the radiation source close to a target region of the living object for directing the emitted radiation to the target region, wherein the living object swells when the placing unit is inserted into the living object,
an imaging unit for generating images of the living object over time,
a processing and control device comprising a non-transitory computer readable storage medium having encoded thereon instructions which when executed by a processor cause:
a spatial parameter determination unit to determine a spatial parameter of the living object, from the generated images of the living object which spatial parameter changes over time with the swelling of the living object,
a treatment time window determination unit to determine a treatment time window, in which a change of the spatial parameter of the living object is minimal,
a planning unit to determine a placing plan defining placing positions within the living object at which the radiation source is to be placed and placing times defining when and how long the radiation source is to be placed at the respective placing position based on the generated images and the determined treatment time window, wherein the planning unit is adapted to determine the placing plan such that the placing times are within the treatment time window.

\* \* \* \* \*